United States Patent
Joseph et al.

(10) Patent No.: US 8,235,917 B2
(45) Date of Patent: Aug. 7, 2012

(54) WIRELESS ELECTROSURGICAL CONTROLLER

(75) Inventors: Daniel A. Joseph, Golden, CO (US); Tatiana E. Zimmerer, Castle Rock, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 679 days.

(21) Appl. No.: 12/353,002

(22) Filed: Jan. 13, 2009

(65) Prior Publication Data

US 2010/0179541 A1    Jul. 15, 2010

(51) Int. Cl.
- A61B 5/103 (2006.01)
- A61B 5/117 (2006.01)
- A61J 17/00 (2006.01)
- A61N 1/00 (2006.01)

(52) U.S. Cl. ......... 600/590; 600/595; 606/234; 607/134
(58) Field of Classification Search ............ 606/41–42, 606/32, 34, 234; 607/134; 600/590, 595, 600/587
See application file for complete search history.

(56) References Cited

U.S. PATENT DOCUMENTS

| | | | |
|---|---|---|---|
| 3,801,766 A | 4/1974 | Morrison, Jr. | |
| 3,935,405 A | 1/1976 | Auer | |
| 4,198,990 A | 4/1980 | Higgins et al. | |
| 4,488,873 A | 12/1984 | Bloomfield et al. | |
| 4,582,057 A | 4/1986 | Auth et al. | |
| 4,728,812 A * | 3/1988 | Sheriff et al. | 307/134 |
| 4,979,516 A | 12/1990 | Abraham, II | |
| 5,078,153 A * | 1/1992 | Nordlander et al. | 600/590 |
| 5,658,322 A | 8/1997 | Fleming | |
| 5,720,742 A | 2/1998 | Zacharias | |
| 6,089,864 A * | 7/2000 | Buckner et al. | 433/71 |
| 6,142,992 A | 11/2000 | Cheng et al. | |
| 6,235,020 B1 | 5/2001 | Cheng et al. | |
| 6,296,636 B1 | 10/2001 | Cheng et al. | |
| 6,306,134 B1 | 10/2001 | Goble et al. | |
| 6,620,189 B1 | 9/2003 | Machold | |
| 6,766,794 B1 | 7/2004 | Bently | |
| 6,837,888 B2 | 1/2005 | Ciarrocca et al. | |
| 6,842,692 B2 | 1/2005 | Fehr et al. | |
| 6,941,952 B1 | 9/2005 | Rush, III | |
| 6,974,453 B2 | 12/2005 | Woloszko et al. | |
| 7,285,117 B2 | 10/2007 | Krueger et al. | |
| 7,375,880 B2 | 5/2008 | Nakamura | |

(Continued)

FOREIGN PATENT DOCUMENTS

DE    179607    3/1905

(Continued)

OTHER PUBLICATIONS

U.S. Appl. No. 12/057,557, filed Mar. 28, 2008.

(Continued)

*Primary Examiner* — Nicholas Lucchesi
*Assistant Examiner* — Rebecca E Eisenberg

(57) ABSTRACT

The present disclosure relates to a wireless, bite activated switch for electrosurgery related electrosurgical systems, and methods of use thereof. During an electrosurgical procedure, a biocompatible switching device is gently held in the surgeon's mouth, typically between the teeth. The surgeon may activate an electrosurgical device by biting down on the switch. In embodiments, the wireless, bite activated switch includes a passive RFID tag that is powered by a radiofrequency signal transmitted by an interrogator included within an electrosurgical system unit. The wireless, bite activated may include a unique identifier which enables the electrosurgical system unit to respond only to a designated wireless device.

20 Claims, 5 Drawing Sheets

U.S. PATENT DOCUMENTS

| | | | | |
|---|---|---|---|---|
| 7,568,619 | B2 * | 8/2009 | Todd et al. | 235/385 |
| 7,675,429 | B2 * | 3/2010 | Cernasov | 340/4.11 |
| 2005/0021020 | A1 * | 1/2005 | Blaha | 606/34 |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4339049 | 5/1995 |
| DE | 19717411 | 11/1998 |
| DE | 19848540 | 5/2000 |
| EP | 246350 | 11/1987 |
| EP | 310431 | 4/1989 |
| EP | 325456 | 7/1989 |
| EP | 390937 | 10/1990 |
| EP | 556705 | 8/1993 |
| EP | 608609 | 8/1994 |
| EP | 836868 | 4/1998 |
| EP | 1051948 | 11/2000 |
| EP | 880220 | 6/2006 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| GB | 607850 | 9/1948 |
| GB | 702510 | 1/1954 |
| GB | 855459 | 11/1960 |
| GB | 902775 | 8/1962 |
| GB | 2164473 | 3/1986 |
| GB | 2214430 | 9/1989 |
| GB | 2358934 | 8/2001 |
| SU | 166452 | 1/1965 |
| SU | 727201 | 4/1980 |

OTHER PUBLICATIONS

U.S. Appl. No. 10/406,690, filed Apr. 3, 2003.
U.S. Appl. No. 11/242,458, filed Oct. 3, 2005.
U.S. Appl. No. 10/573,713, filed Mar. 28, 2006.
U.S. Appl. No. 12/136,620, filed Jun. 10, 2008.
U.S. Appl. No. 12/389,168, filed Feb. 19, 2009.
U.S. Appl. No. 12/351,935, filed Jan. 12, 2009.
U.S. Appl. No. 12/401,981, filed Mar. 11, 2009.
U.S. Appl. No. 12/351,947, filed Jan. 12, 2009.
U.S. Appl. No. 12/407,896, filed Mar. 20, 2009.
U.S. Appl. No. 12/205,525, filed Sep. 5, 2008.
U.S. Appl. No. 12/249,263, filed Oct. 10, 2008.
U.S. Appl. No. 12/249,218, filed Oct. 10, 2008.
U.S. Appl. No. 12/351,970, filed Jan. 12, 2009.
U.S. Appl. No. 12/351,960, filed Jan. 12, 2009.
U.S. Appl. No. 12/205,298, filed Sep. 5, 2008.
U.S. Appl. No. 12/351,980, filed Jan. 12, 2009.
U.S. Appl. No. 12/203,734, filed Sep. 3, 2008.
U.S. Appl. No. 12/242,102, filed Sep. 30, 2008.
U.S. Appl. No. 12/241,861, filed Sep. 30, 2008.
U.S. Appl. No. 12/242,061, filed Sep. 30, 2008.
U.S. Appl. No. 12/242,026, filed Sep. 30, 2008.
U.S. Appl. No. 12/241,905, filed Sep. 30, 2008.
U.S. Appl. No. 12/241,942, filed Sep. 30, 2008.
U.S. Appl. No. 12/241,983, filed Sep. 30, 2008.
Wald et al., "Accidental Burns", JAMA, Aug. 16, 1971, vol. 217, No. 7, pp. 916-921.
Vallfors et al., "Automatically Controlled Bipolar Electrosoagulation—'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" in William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.

International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.

* cited by examiner

FIG. 2A     FIG. 2C

WIRELESS ELECTROSURGICAL CONTROLLER

BACKGROUND

1. Technical Field

The present disclosure relates to electrosurgical systems and more particularly, a wireless bite-activated control device for controlling electrosurgical generators, electrosurgical instruments, and systems related thereto.

2. Background of Related Art

Minimally invasive surgical techniques have been developed wherein the surgical site is accessed by instruments inserted through small incisions in the body, as compared to traditional open surgical procedures where much larger incisions are required to expose the surgical site. Minimally invasive surgical procedures, also known generally as laparoscopic or endoscopic procedures, are often performed in conjunction with electrosurgical techniques. Throughout the present disclosure, the term "minimally invasive" should be understood to encompass both endoscopic and laparoscopic procedures, and the terms "minimally invasive", "endoscopic", and "laparoscopic" are to be construed equivalently. Minimally invasive surgical procedures are performed through access devices such as a cannula that is inserted percutaneously into a patient's body. The cannula has a central opening through which surgical objects are introduced and manipulated during the course of the procedure.

Electrosurgical techniques employ radiofrequency (RF) electrical signals in the approximately 200 kHz-3.3 mHz range in connection with surgical instruments, to cut, ablate, or coagulate biologic tissue endogenically. Typically, electrosurgical signals are operated at 100% duty cycle for maximal cutting effect, and are pulse modulated at duty cycles ranging from 50% to 25% for less aggressive cutting, also referred to as blending, or, at a substantially lower duty cycle of approximately 6%, for coagulating. The electrosurgical signal can be applied to the patient via electrodes in either bipolar mode, or monopolar mode. In bipolar mode, both the active and return electrodes are at the surgical site, effectuated by, for example, both jaws of a pair of forceps, such that the electrosurgical signal passes through only the tissue that is held between the jaws of the instrument. In monopolar mode, the active electrode is the surgical instrument at the surgical site, and the return electrode is elsewhere on the patient, such that the electrosurgical signal passes through the patient's body from the surgical site to the return electrode.

Typically, the instrument has at a distal end thereof an end effector, such as a blade, forceps, snare, loop, or suction coagulator, that is positioned at the surgical site. The proximal end of the instrument is coupled to a source of electrosurgical energy, such as an electrosurgical generator. After the instrument is positioned, the surgeon actuates a control, typically a handswitch on the instrument, or a footswitch, which causes electrosurgical energy to be applied through the end effector to the operative site to tissue to achieve a desired result, e.g., cutting, coagulating, ablation, or fusion. Often, requirements of a surgical procedure dictate that a surgeon manipulate one or more instruments using both hands.

SUMMARY

The present disclosure provides a wireless switch having a resilient housing for actuation by a user, such as a surgeon, during for example, an electrosurgical procedure. The disclosed switch may be bite-activated. The switch includes an activator, such as without limitation, a pushbutton, disposed within the housing and activatable in response to a compressive force applied to at least one of the top surface and the bottom surface, e.g., in response to biting force. The disclosed switch further includes an antenna configured to at least one of transmit and receive a radiofrequency signal. The antenna may be adapted to connect to a transponder included within the switch that is configured to receive a radiofrequency interrogatory signal. In response to the radiofrequency interrogatory signal the transponder senses the state of the activator (e.g., whether the activator is activated/pressed or deactivated/released) and transmits a radiofrequency response signal conveying the state of the activator to an electrosurgical energy source.

In embodiments, the activator may include conductive resilient material, such as without limitation electrically-conductive silicone. In embodiments, the activator may include a snap dome switch, membrane switch, pushbutton switch, or other suitable switch.

In another aspect, an electrosurgical system is provided that includes an electrosurgical system unit. The electrosurgical system unit includes an interrogator adapted to communicate with a bite-activated wireless switch as described herein. In use, the interrogator transmits a radiofrequency interrogatory signal to the transponder included in the bite-activated switch. The transponder responds by sensing the state of the activator included within the wireless switch assembly (e.g., whether the surgeon is biting down on the switch) and transmitting a signal to the interrogator conveying the switch state. The electrosurgical system unit may include a controller, which may include a processor, for performing a set of executable instructions for performing, at least in part, a method of electrosurgery using a wireless bite-activated switch as disclosed herein. The electrosurgical system unit further includes an electrosurgical instrument coupled to an electrosurgical generator configured to selectively provide electrosurgical energy thereto, and a user interface, such as without limitation, input controls and output indicators, to facilitate interaction with the user e.g., the surgeon.

In yet another aspect, the present disclosure provides a method for performing electrosurgery. The disclosed method includes the steps of providing a bite-activated wireless switch as disclosed herein, providing an electrosurgical system unit as disclosed herein, causing to be transmitted an interrogatory signal to a transponder included within the bite-activated wireless switch, receiving the interrogatory signal at the transponder, causing to be transmitted in response the interrogatory signal a response signal conveying the state of the pushbutton; receiving the response signal at the electrosurgical system unit, activating the electrosurgical generator in response to a response signal conveying an actuated pushbutton state, and deactivating the electrosurgical generator in response to a response signal conveying a de-actuated pushbutton state.

The present disclosure further provides a method of activating the source of electrosurgical energy wherein a first activation of a wireless switch activates the electrosurgical generator and a second activation of a wireless switch deactivates the electrosurgical generator (e.g., a push-on/push-off mode of operation). In another embodiment, a single activation of the wireless switch causes the electrosurgical generator to be activated for a predetermined period of time, after which the electrosurgical generator automatically is deactivated. Other embodiments are contemplated wherein the electrosurgical generator is deactivated if the wireless switch is activated before the fixed period of activation time elapses.

In this embodiment, the disclosed system operates in a primarily push-on/push-off mode with a safety timeout feature.

In still another aspect, the present disclosure provides a method of associating a bite-activated wireless switch with an electrosurgical system unit that includes the steps of providing a unique identifier for the bite-activated switch, transmitting in response to an interrogatory signal a response signal conveying the unique identifier of the bite-activated switch to the electrosurgical system unit, storing the unique identifier of the bite-activated switch, comparing the stored unique identifier to a unique identifier conveyed in a subsequent response signal, and ignoring a subsequent response signal if the unique identifier thereof differs from the stored unique identifier.

BRIEF DESCRIPTION OF THE DRAWINGS

The above and other aspects, features, and advantages of the present disclosure will become more apparent in light of the following detailed description when taken in conjunction with the accompanying drawings wherein:

FIG. 2A is a top, side view of an embodiment of a wireless bite-activated switch in accordance with the present disclosure;

FIG. 2C is a right, side view of an embodiment of a wireless bite-activated switch in accordance with the present disclosure;

DETAILED DESCRIPTION

Figure 1:
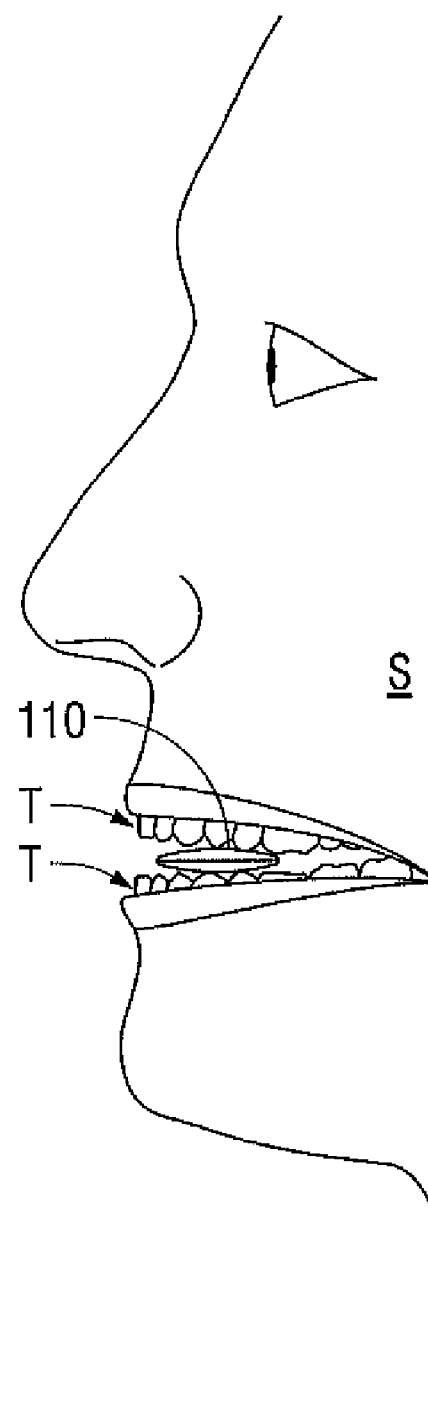
FIG. 1 is a schematic view of an embodiment of a wireless bite-activated switch in accordance with the present disclosure.

Particular embodiments of the present disclosure will be described hereinbelow with reference to the accompanying drawings; however, it is to be understood that the disclosed embodiments are merely exemplary of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, shall refer to the end of the instrument that is closer to the user, while the term "distal" shall refer to the end that is farther from the user.

Figure 2B:
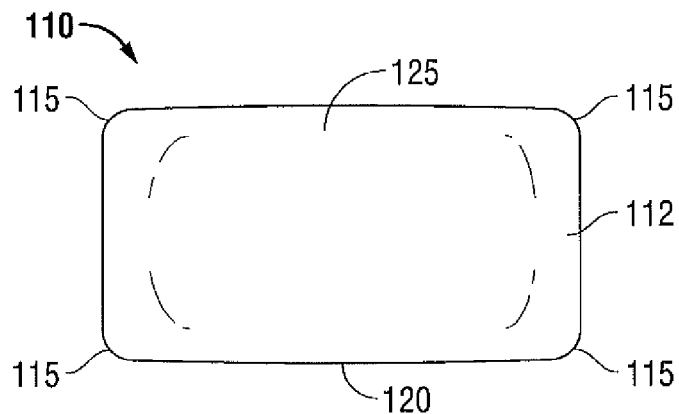
FIG. 2B is a front, side view of an embodiment of a wireless bite-activated switch in accordance with the present disclosure.
Figure 2B:
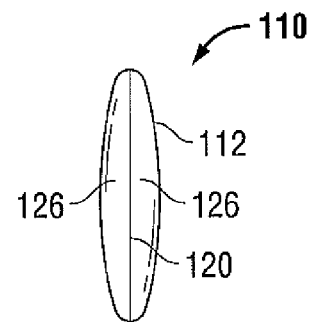
Figure 2B:
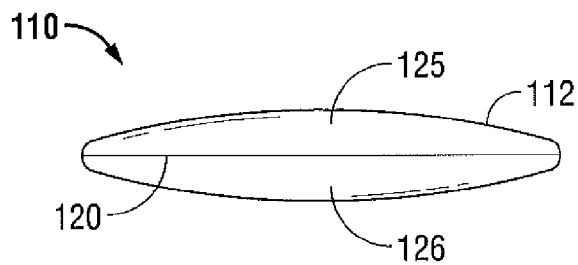
Figure 2D:
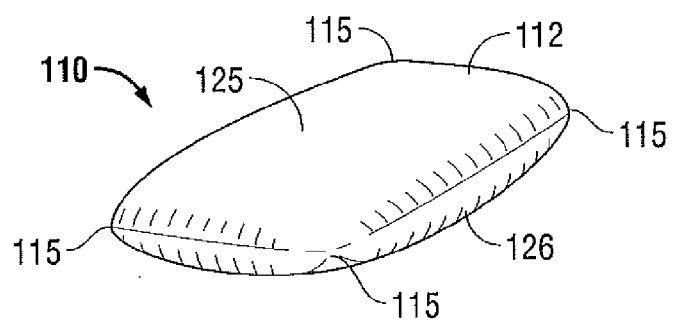
FIG. 2D is a perspective view of an embodiment of a wireless bite-activated switch in accordance with the present disclosure.

With reference to FIG. 1 and FIGS. 2A-2D, a bite-activated wireless switch 110 is held between the teeth T of a surgeon S. Wireless switch 110 includes a housing 112 having an upper cover 125 and a lower cover 126. In some embodiments, housing 112 has a generally pillow-like rectangular shape having radiused corners 115 as best illustrated in FIG. 2A. The present disclosure also contemplates that housing 112 may be any shape, including without limitation circular, oval, and crescent-shaped. In embodiments, housing 112 is formed from a resilient or elastomeric material, such as without limitation, vinyl, rubber, silicone, thermoplastic elastomer (e.g., C-Flex®), polyurethane, or polypropylene. Housing 112 may be formed from biocompatible material suitable for use within the mouth and/or capable of uncompromised passage through a digestive tract in the event the wireless switch 110 is ingested.

In embodiments, upper cover 125 and lower cover 126 are joined at the respective perimeters thereof by seam 120, which may be formed by any suitable manner of bonding, e.g., heat welding, ultrasonic welding, chemical welding, adhesive, and the like. In embodiments, upper cover 125 and lower cover 126 may be formed integrally. In embodiments upper cover 125 and/or lower cover 126 may have a textured surface (not explicitly shown) adapted to facilitate placement and retention of wireless switch 110 within the mouth and/or jaw of the user. In embodiments, the textured surface may be contoured to engage at least one of the user's teeth. Wireless switch 110 may be reusable, disposable, or partially disposable. In embodiments, the housing 112 is flavored, e.g., mint-flavored, chocolate-flavored, fruit-flavored, and so forth.

Figure 3A:
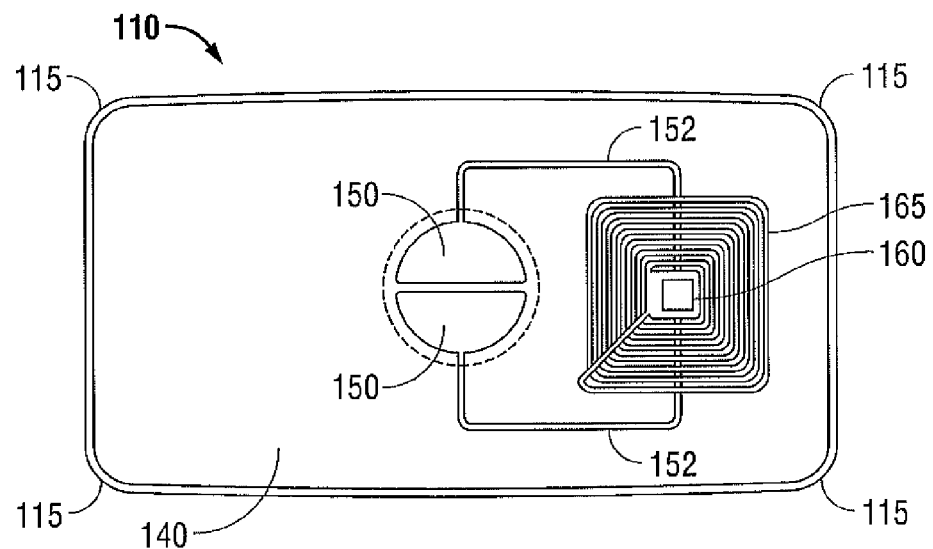
FIG. 3A is a top, cutaway view of an embodiment of a wireless bite-activated switch in accordance with the present disclosure.
Figure 3B:
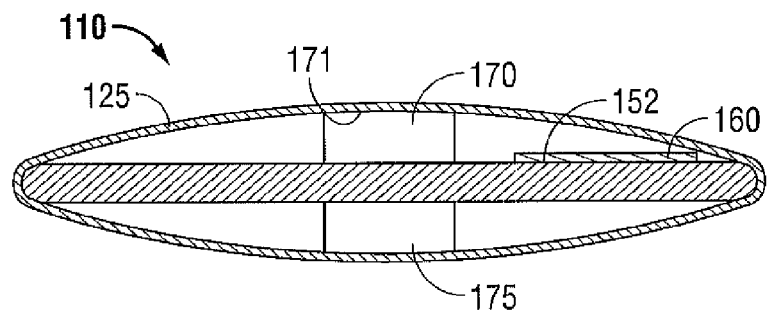
FIG. 3B is a front, cutaway view of an embodiment of a wireless bite-activated switch in a quiescent state in accordance with the present disclosure.

With reference now to FIGS. 3A and 3B, wireless switch 110 includes a support member 140 disposed within the housing 112. In embodiments, support member 140 may be a circuit board constructed of any suitable material, for example without limitation, phenolic cotton paper (e.g., FR-2), cotton paper and epoxy (e.g., FR-3, CEM-1, CEM-2), woven glass and epoxy (e.g., FR-4, FR-5, G-10, CEM-3, CEM-4), matte glass and polyester (FR-6), or woven glass and polyester (CEM-5).

Support member 140 includes transponder 160 that is operably coupled to antenna 165 and contacts 150. In embodiments, transponder 160 may be an integrated circuit, such as without limitation, an RFID tag. Advantageously, transponder 160 may be a passive RFID tag that is powered by the electrical current induced in antenna 165 by the radiofrequency interrogation signal. Transponder 160 may contain read-only data, such as without limitation, a unique identifier, a model number, a compatibility identifier, and/or an expiration date. Such read-only data may be stored in an encrypted format. In embodiments, transponder 160 is operably coupled to contacts 150 by conductors 152. Contacts 150 are in operable communication with pushbutton 170 to communicate the activation state of pushbutton 170 to transponder 160. Pushbutton 170 may be a momentary contact switch, or a toggle contact switch (e.g., push on/push off). In embodiments, pushbutton 170 is formed from resilient conductive material, such as without limitation graphite-impregnated silicone that is adapted to cause, in response to compressive force applied to pushbutton 170, and/or top surface 171 of pushbutton 170, a change in resistance, e.g., a decrease in resistance, in a conductive path formed by contacts 150 and pushbutton 170. In embodiments, pushbutton 170 is configured to provide tactile feedback to the user, for example without limitation, a clicking, snapping, or vibratory sensation. Wireless switch 110 may include a resilient member 175 configured to act as a counterpart to pushbutton 170 and provide a generally equal distribution of bite forces imposed on housing 125 and/or wireless switch 110. In embodiments, resilient member 175 may be a switch (e.g., a pushbutton) to provide, for example without limitation, redundancy with pushbutton 170, or to provide additional or alternative sensing modalities (e.g., increased pressure sensing range, and/or sensing related to side-to-side jaw motion). In embodiments, resilient member may be operatively coupled to pushbutton 170 and/or transponder 160 via conductors (not explicitly shown).

In embodiments, wireless switch 110 includes a power source (not explicitly shown), such as without limitation, a battery, a saline fuel cell, or a thermoelectric device. In embodiments, the power source may be initially provided in an inactive state, for example, during manufacture, shipping, and storage. It in envisioned the power source may be activated prior to using the wireless switch by the first application of force sufficient to compress and/or deform resilient housing 112, as further described hereinbelow.

Figure 3C:
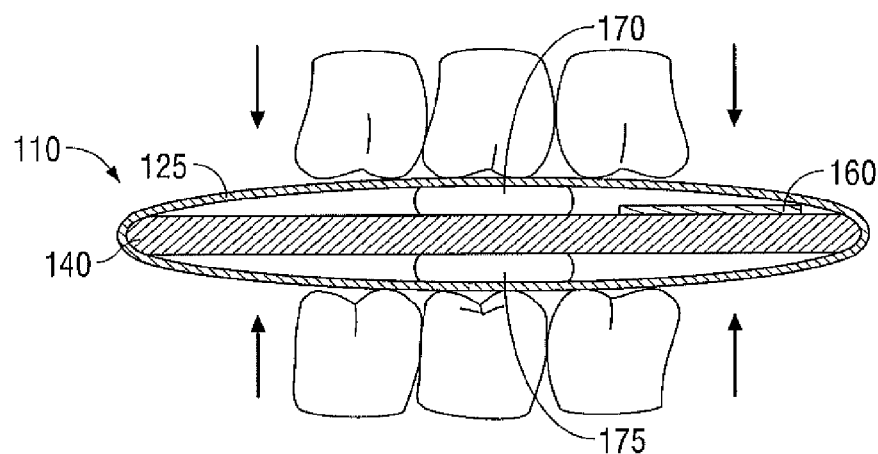
FIG. 3C is a front, cutaway view of an embodiment of a wireless bite-activated switch in an activated state in accordance with the present disclosure.
Figure 4:
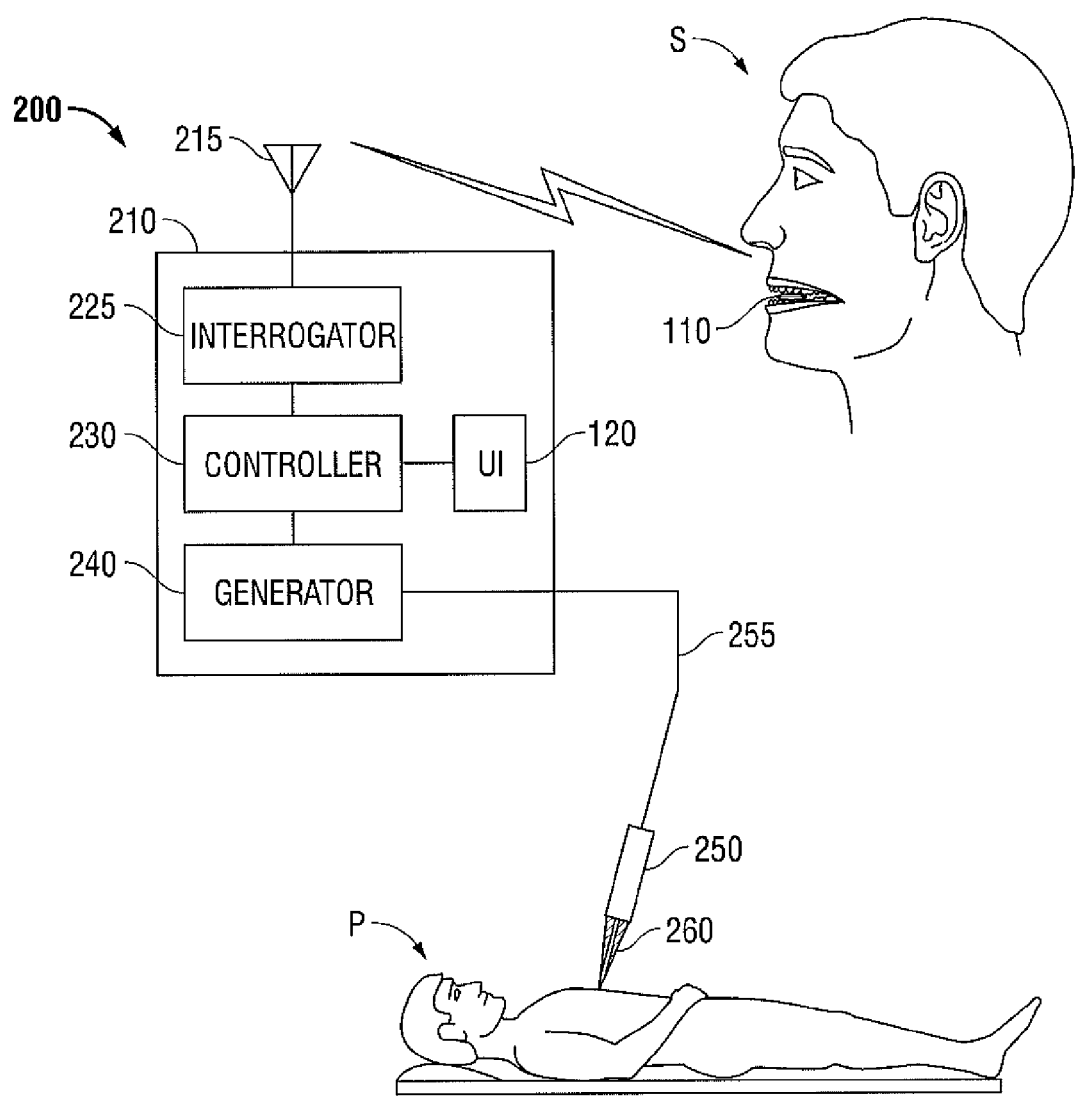
FIG. 4 is a schematic view of an electrosurgical system having an embodiment of a wireless bite-activated switch in accordance with the present disclosure.

In use, e.g., during an electrosurgical procedure, wireless switch 110 may be held between the user's teeth, e.g., between the maxillary and mandibular teeth of the user (e.g., the surgeon). Initially, wireless switch 110 may be held between the teeth using minimal force, e.g., force sufficient to retain wireless switch 110 in place without significant compression and/or deformation of resilient housing 112. Thereafter, the user may bite down on wireless switch 110 using increased force, e.g., force sufficient to compress and/or deform resilient housing 112, which in turn activates pushbutton 170 as best illustrated in FIG. 3C. In response, transponder 160 communicates the switch state to an interrogator 225 included in an electrosurgical system unit 210 (described hereinbelow) which consequently activates an RF generator 240 that is operably coupled to an electrosurgical instrument 250 to deliver electrosurgical energy to tissue. In embodiments, the pushbutton 170 is configured to sense and/or measure continuous pressure imposed thereon and convey a signal proportionate thereto.

In another aspect, the present disclosure provides an electrosurgical system 200 having an electrosurgical system unit 210 that includes a controller 230 in operative communication with an interrogator 225, a generator 240, and a user interface 220. Controller 230 may include a processor (not explicitly shown) for executing a set of program instructions stored in memory (not explicitly shown) such as without limitation, SRAM, DRAM, flash memory, disk memory, EEPROM, or any other suitable memory now or in the future known. Additionally or alternatively, controller 230 may include a suitable analog circuit. Electrosurgical system unit 210 includes a user interface 220 which may include an input control (e.g., hand-switch, footswitch, rotary control, button, touchscreen, and the like), output indicators (e.g., visual displays, audio tones, haptic devices, and the like).

Electrosurgical system unit 210 includes a generator 240 that is configured to deliver electrosurgical energy to electrosurgical instrument 250. Generator 240 and/or electrosurgical instrument 250 may be configured for monopolar and/or bipolar modes of operation. Electrosurgical system unit 210 includes a controller 230 that is configured and/or programmed to control the operation of generator 240, including without limitation the intensity, duration, and waveshape of the generated electrosurgical energy, and/or accepting input, such as without limitation user input and sensor input. Generator 240 may generate any suitable energy, such as without limitation RF (radio frequency), microwave, ultrasound, infrared, ultraviolet, laser, thermal energy or other energy.

Generator 240 may be operably coupled to electrosurgical instrument 250 by cable 255, which includes at least one conductor (not explicitly shown). In embodiments, cable 255 may couple a sensor (not explicitly shown) included in electrosurgical instrument 250 to generator 240 configured to convey a biological property at the operative site, for example without limitation, temperature, pressure, and/or impedance, to electrosurgical system unit 210. It is contemplated that generators such as those sold by Valleylab, a division of Covidien, located in Boulder, Colo. may be used as a source of electrosurgical energy, e.g., Ligasure® Generator, FORCE EZ® Electrosurgical Generator, FORCE FX® Electrosurgical Generator, FORCE 1C™, FORCE 2™ Generator, SurgiStat® II, FORCETRIAD® or other envisioned generators which may perform different or enhanced functions. One such system is described in commonly-owned U.S. Pat. No. 6,033,399 entitled "ELECTROSURGICAL GENERATOR WITH ADAPTIVE POWER CONTROL." Other systems have been described in commonly-owned U.S. Pat. No. 6,187,003 entitled "BIPOLAR ELECTROSURGICAL INSTRUMENT FOR SEALING VESSELS."

Electrosurgical system unit 210 includes an interrogator 225 and antenna 215 configured to wirelessly communicate with transponder 160. In use, electrosurgical system unit 210 may be powered up by a user (e.g., typically, a surgeon or clinician). The controller 230 may perform a power-on self test (POST) to verify proper operation of electrosurgical system unit 210. In one aspect, electrosurgical system unit 210 may be operably associated (e.g., "married") with a unique wireless switch 110 such that wireless activation of electrosurgical system unit 210 is only possible by actuation of a designated unique wireless switch 110. Such association may be desirable to eliminate the risk of inadvertent actuation by a superfluous wireless switch 110 that may be within operating proximity of electrosurgical system unit 210 (e.g., present in an adjacent operating room, for example). In embodiments, a wireless switch 110 may be associated with electrosurgical system unit 210 by a "marrying" process consisting of receiving a user input indicating the marrying process is to be initiated, transmitting an identification request from the interrogator 225 to a wireless switch 110, responding to the identification request by transmitting from the wireless switch 110 an identification response, and storing the identification response. In embodiments, the marrying process may include the steps of actuating the wireless switch 110 in a predetermined manner, such as without limitation, three actuations within a three seconds period of time, or, as another example, one long actuation having a duration of about one second, followed by one short actuation having a duration of about one-quarter of a second, followed by one long actuation having a duration of about one second.

In embodiments, the electrosurgical system unit 210 is selectively operable in a standby mode or an active mode. In standby mode, the activation of electrosurgical RF generator 240 is inhibited, e.g., actuation of wireless switch 110 will not cause activation of electrosurgical RF generator 240 and/or electrosurgical energy. In embodiments, actuation of wireless switch 110 while electrosurgical system unit 210 is in a standby mode will cause an output indication e.g., a visual, audio, or tactile indication. Such an indication may allow to user to confirm operation of the system (e.g., that the wireless switch 110 was successfully "married" to the electrosurgical system unit 210) prior to commencement of surgery. In active mode, actuation of wireless switch 110 causes activation of electrosurgical RF generator 240 and/or electrosurgical energy. In embodiments, actuation of wireless switch 110 while electrosurgical system unit 210 is in an active mode will cause an output indication e.g., a visual, audio, or tactile indication. In embodiments, an output indication issued while in standby mode is distinct from an output indication issued while in active mode. By way of example only, a standby mode actuation indication may be characterized by a pulsed beep tone, while an active mode actuation indication may be characterized by a continuous beep tone.

In one aspect, interrogator 225 may communicate with transponder 160 in a continuous poll and response fashion. An interrogation signal is communicated from interrogator 225 to wireless switch 110 (e.g., polling). The interrogation signal is received by antenna 165 and consequently delivered to transponder 160. In embodiments, the interrogation signal includes an identifier derived at least in part from the association (e.g., "marrying") procedure previously described. In response to an interrogation signal, transponder 160 senses the state of switch 170, and generates a response signal that conveys the switch state (e.g., the response). The response signal is received by antenna 215 and communicated to interrogator 225, which, in turn, conveys the switch status to controller 230. The poll and response cycle may repeat iteratively. In embodiments, the poll and response cycle repeats at a rate in the range of about once per second to about a thousand times per second. In embodiments, the poll and response cycle repeats at a rate of about one hundred time per second. Advantageously, the poll and response cycle is repeated such that system latency is negligible, e.g., a delay between actuating/deactuating switch 170 and the corresponding activation/deactivation of generator 240 is imperceptible to the surgeon, and/or clinically unremarkable. In embodiments, at least part of the energy of the interrogation signal induces an electrical current in antenna 165 sufficient to power transponder 160.

In embodiments, interrogator 225 and antenna 215 may be included within electrosurgical system unit 210. In yet other envisioned embodiments, interrogator 225 and antenna 215 may configured as an independent unit adapted to interoperate with existing electrosurgical generators (e.g., in a piggyback or retro-fit configuration).

Figure 5A:
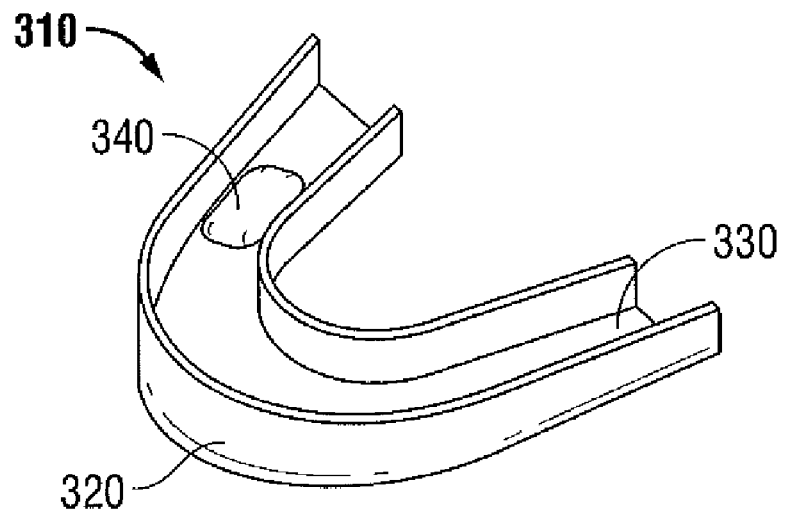
FIG. 5A is a perspective view of yet another embodiment of a wireless bite-activated switch in accordance with the present disclosure.
Figure 5B:
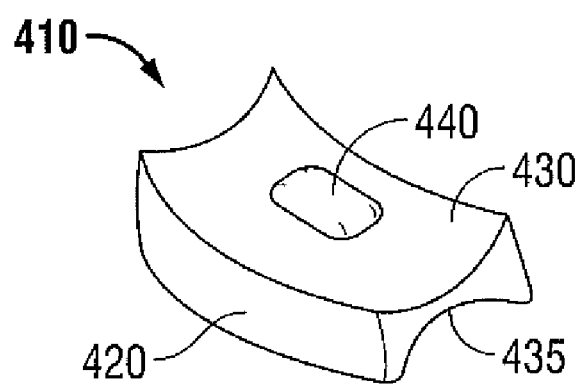
FIG. 5B is a perspective view of still another embodiment of a wireless bite-activated switch in accordance with the present disclosure.

Turning now to FIG. 5A, an embodiment of a bite-activated wireless switch 310 in accordance with the present disclosure includes a housing 340 that is included in a substantially mouthguard-shaped support 320. In embodiments, the mouthguard-shaped support 320 may be custom-fitted to a user's mouth, incorporating, for example, a custom-fitted biting surface 330 formed from an impression of the user's teeth. Housing 340 may be integrally formed with mouthguard-shaped support 320, or, alternatively, housing 340 may be detachably coupled to mouthguard-shaped support 320. FIG. 5B illustrates yet another embodiment of a bite-activated wireless switch 410 in accordance with the present disclosure that includes a housing 440 that is included in support member 420 that is contoured in a truncated mouthguard-like shape that is adapted to be held between, for example, the user's maxillary and mandibular incisors, canines, or molars.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A wireless switch, comprising:
    a resilient housing having a top surface and a bottom surface configured for insertion within a user's mouth;
    an activator disposed within the housing and activatable in response to a force applied to at least one of the top surface and the bottom surface;
    an antenna configured to at least one of transmit and receive a radiofrequency signal, the antenna adapted to connect to a transponder, wherein the transponder receives a radiofrequency interrogation signal including an identifier, and, in response thereto, senses the state of the activator, and wherein the transponder transmits a radiofrequency response signal conveying the state of the activator to an electrosurgical energy source.

2. The wireless switch in accordance with claim 1, wherein the activator includes conductive resilient material.

3. The wireless switch in accordance with claim 1, wherein the activator is configured to provide tactile feedback upon activation.

4. The wireless switch in accordance with claim 1, wherein the activator is activatable in response to a compressive force applied to at least one of the top surface and the bottom surface.

5. The wireless switch in accordance with claim 1, wherein the resilient housing is formed from material selected from the group consisting of vinyl, rubber, silicone, thermoplastic elastomer, polyurethane, and polypropylene.

6. The wireless switch in accordance with claim 1, wherein the resilient housing includes a flavoring.

7. The wireless switch in accordance with claim 1, wherein the transponder is further configured to transmit a unique identifier in response to a radiofrequency interrogatory signal.

8. A wireless switch, comprising:
    a resilient housing having a top surface and a bottom surface;
    an actuator disposed within the housing and activatable in response to a force applied to at least one of the top surface and the bottom surface;
    an antenna for transmitting and receiving a radiofrequency signal;
    a transponder operatively coupled to the activator and the antenna, wherein the transponder receives a radiofrequency interrogation signal including an identifier, and in response thereto, senses the state of the activator, and the transponder transmits a radiofrequency response signal conveying the state of the activator.

9. The wireless switch in accordance with claim 8, wherein the transponder includes an RFID tag.

10. The wireless switch in accordance with claim 8, wherein the transponder is powerable by an electric current induced by the radiofrequency interrogatory signal.

11. The wireless switch in accordance with claim 8, further comprising a power source operably coupled to the transponder.

12. The wireless switch in accordance with claim 8, wherein the transponder is further configured to transmit a unique identifier in response to a radiofrequency interrogatory signal.

13. The wireless switch in accordance with claim 8, wherein the resilient housing is formed from material selected from the group consisting of vinyl, rubber, silicone, thermoplastic elastomer, polyurethane, and polypropylene.

14. The wireless switch in accordance with claim 8, wherein the resilient housing includes a flavoring.

15. An electrosurgical system, comprising:
- an electrosurgical system unit comprising in operative communication:
  - an interrogator adapted to at least one of transmit a radiofrequency interrogation signal to a wireless switch or receive a radiofrequency response signal from a wireless switch;
  - a controller;
  - an electrosurgical energy source configured to selectively provide electrosurgical energy; and
  - a user interface;
- a wireless switch, comprising:
  - a resilient housing having a top surface and a bottom surface configured for insertion within a user's mouth;
  - an activator disposed within the housing and activatable in response to a force applied to at least one of the top surface and the bottom surface;
  - an antenna configured to at least one of transmit and receive a radiofrequency signal, the antenna adapted to connect to a transponder, wherein the transponder receives a radiofrequency interrogation signal including an identifier, and, in response thereto, senses the state of the activator, and wherein the transponder transmits a radiofrequency response signal conveying the state of the activator to an electrosurgical energy source; and
- an electrosurgical instrument operably coupled to the electrosurgical energy source.

16. The electrosurgical system according to claim 15, wherein activation of the wireless switch activates the electrosurgical energy source.

17. The electrosurgical system according to claim 16, wherein the electrosurgical system unit has a first operating mode and a second operating mode.

18. The electrosurgical system according to claim 17, wherein:
- in the first operating mode, activation of the wireless switch causes to be generated an output indication; and
- in the second operating mode, activation of the wireless switch activates the electrosurgical energy source.

19. The electrosurgical system according to claim 15, wherein:
- a first activation of the wireless switch causes the electrosurgical energy source to be activated; and
- a second activation of the wireless switch causes the electrosurgical energy source to be deactivated.

20. The electrosurgical system according to claim 15, wherein:
- activation of the wireless switch causes the electrosurgical energy source to be activated for a predetermined period of time.

* * * * *